(12) United States Patent
Lamoureux et al.

(10) Patent No.: US 7,878,964 B1
(45) Date of Patent: Feb. 1, 2011

(54) ECHOGENIC SPACERS AND STRANDS

(75) Inventors: Gary A. Lamoureux, Woodbury, CT (US); Warren W. Johnston, Thomaston, CT (US)

(73) Assignee: Biocompatibles UK Limited, Farnham, Surrey (GB)

( * ) Notice: Subject to any disclaimer, the term of this patent is extended or adjusted under 35 U.S.C. 154(b) by 966 days.

(21) Appl. No.: 11/517,642

(22) Filed: Sep. 7, 2006

(51) Int. Cl.
 *A61M 36/00* (2006.01)
(52) U.S. Cl. .............................................. 600/7; 600/8
(58) Field of Classification Search ................. 600/1–8; 606/228–231
 See application file for complete search history.

(56) References Cited

U.S. PATENT DOCUMENTS

| | | | |
|---|---|---|---|
| 1,578,945 A | 3/1926 | Withers | |
| 2,067,589 A | 1/1937 | Antrim | |
| 2,153,889 A * | 4/1939 | Hames | 600/3 |
| 2,703,316 A | 6/1951 | Schneider | |
| 2,575,138 A | 11/1951 | Slaughter | |
| 2,758,987 A | 6/1952 | Salzberg | |
| 2,668,162 A | 2/1954 | Lowe | |
| 3,297,033 A | 10/1963 | Schmidt et al. | |
| 3,187,752 A * | 6/1965 | Glick | 606/231 |
| 3,351,049 A | 11/1967 | Lawrence | |
| 3,565,869 A | 2/1971 | De Prospero | |
| 3,636,956 A | 1/1972 | Schneider | |
| 3,752,630 A | 8/1973 | Takagi | |
| 3,811,426 A | 5/1974 | Culver et al. | |
| 3,839,297 A | 10/1974 | Wasserman et al. | |
| 3,936,414 A | 2/1976 | Wright et al. | |
| 4,052,988 A | 10/1977 | Doddi | |
| 4,086,914 A | 5/1978 | Moore | |
| 4,141,087 A | 2/1979 | Shalaby et al. | |
| 4,167,179 A | 9/1979 | Kirsch | |
| 4,402,308 A | 9/1983 | Scott | |
| 4,416,659 A | 11/1983 | Simpson et al. | |
| 4,441,496 A | 4/1984 | Shalaby et al. | |
| 4,452,973 A | 6/1984 | Casey et al. | |
| 4,473,670 A | 9/1984 | Kessidis | |

(Continued)

FOREIGN PATENT DOCUMENTS

EP 0 030 822 B1 9/1983

(Continued)

OTHER PUBLICATIONS

Amersham Health; "OncoSeed Indications"; http://www.amershamhealth-us.com/oncoseed/; printed Nov. 19, 2003.

(Continued)

*Primary Examiner*—Charles A Marmor, II
*Assistant Examiner*—Carrie Dorna
(74) *Attorney, Agent, or Firm*—Fliesler Meyer LLP

(57) ABSTRACT

Echogenic strands and spacers are provided for use in brachytherapy. Methods of making the strands and spacers are also provided. An echogenic strand for use in brachytherapy and a method for making the strand includes an encapsulating material, a seed disposed within the encapsulating material, and a spacer disposed within the encapsulating material and arranged adjacent to the seed. The spacer has an axial length, an outer surface and an inner surface. A chamber is formed along the axial length, the chamber being defined by the inner surface. The chamber is adapted to improve ultrasound visibility relative to the spacer.

31 Claims, 4 Drawing Sheets

U.S. PATENT DOCUMENTS

| | | |
|---|---|---|
| 4,509,506 A | 4/1985 | Windorski et al. |
| 4,510,295 A | 4/1985 | Bezwada et al. |
| 4,612,923 A | 9/1986 | Kronenthal |
| 4,646,741 A | 3/1987 | Smith |
| 4,689,424 A | 8/1987 | Shalaby et al. |
| 4,697,575 A | 10/1987 | Horowitz |
| 4,702,228 A | 10/1987 | Russell et al. |
| 4,741,337 A | 5/1988 | Smith |
| 4,754,745 A | 7/1988 | Horowitz |
| 4,772,287 A | 9/1988 | Ray et al. |
| 4,784,116 A | 11/1988 | Russell, Jr. et al. |
| 4,815,449 A | 3/1989 | Horowitz |
| 4,847,505 A | 7/1989 | Suthanthiran |
| 4,891,165 A | 1/1990 | Suthanthiran |
| 4,916,209 A | 4/1990 | Fung et al. |
| 4,936,823 A | 6/1990 | Colvin et al. |
| 4,946,435 A | 8/1990 | Suthanthiran et al. |
| 5,022,940 A | 6/1991 | Mehoudar |
| 5,242,373 A | 9/1993 | Scott et al. |
| 5,264,540 A | 11/1993 | Cooper et al. |
| 5,339,812 A | 8/1994 | Hardy et al. |
| 5,391,139 A | 2/1995 | Edmundson |
| 5,397,816 A | 3/1995 | Reilly et al. |
| 5,403,576 A | 4/1995 | Lin et al. |
| 5,405,309 A | 4/1995 | Carden, Jr. |
| 5,460,592 A | 10/1995 | Langton et al. |
| 5,521,280 A | 5/1996 | Reilly et al. |
| 5,713,828 A | 2/1998 | Coniglione |
| 5,755,704 A | 5/1998 | Lunn |
| 5,761,877 A | 6/1998 | Quandt |
| 5,833,593 A | 11/1998 | Liprie |
| 5,860,909 A | 1/1999 | Mick et al. |
| 5,928,130 A | 7/1999 | Schmidt |
| 5,938,583 A | 8/1999 | Grimm |
| 6,007,475 A | 12/1999 | Slater et al. |
| 6,010,446 A | 1/2000 | Grimm |
| 6,039,684 A | 3/2000 | Ildstad et al. |
| 6,053,858 A | 4/2000 | Bueche et al. |
| 6,080,099 A | 6/2000 | Slater et al. |
| 6,086,942 A | 7/2000 | Carden, Jr. et al. |
| 6,099,457 A | 8/2000 | Good |
| 6,132,359 A | 10/2000 | Bolenbaugh |
| 6,132,677 A | 10/2000 | Ohriner |
| 6,132,947 A | 10/2000 | Honan et al. |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater et al. |
| 6,213,932 B1 | 4/2001 | Schmidt |
| 6,248,057 B1 | 6/2001 | Mavity et al. |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 | 9/2001 | Keren |
| 6,312,374 B1 | 11/2001 | von Hoffmann |
| 6,319,190 B1 | 11/2001 | Schmidt et al. |
| 6,327,490 B1 | 12/2001 | Spetz |
| 6,358,195 B1 | 3/2002 | Green et al. |
| 6,360,116 B1 | 3/2002 | Jackson, Jr. et al. |
| 6,387,034 B1 | 5/2002 | Lee |
| 6,398,709 B1 | 6/2002 | Ehr et al. |
| 6,403,916 B1 | 6/2002 | Spooner et al. |
| 6,419,621 B1 | 7/2002 | Sioshansi et al. |
| 6,428,504 B1 | 8/2002 | Riaziat et al. |
| 6,436,026 B1 | 8/2002 | Sioshansi et al. |
| 6,438,401 B1 | 8/2002 | Cheng et al. |
| 6,450,937 B1 | 9/2002 | Mercereau et al. |
| 6,450,938 B1 | 9/2002 | Miller |
| 6,450,939 B1 | 9/2002 | Grimm |
| 6,471,631 B1 | 10/2002 | Slater et al. |
| 6,472,675 B2 | 10/2002 | White et al. |
| 6,474,535 B1 | 11/2002 | Shanks et al. |
| 6,482,178 B1 | 11/2002 | Andrews et al. |
| 6,497,646 B1 | 12/2002 | Candelaria et al. |
| 6,500,109 B2 | 12/2002 | Tokita et al. |
| 6,514,193 B2 | 2/2003 | Kaplan |
| 6,537,192 B1 | 3/2003 | Elliott et al. |
| 6,537,193 B1 | 3/2003 | Lennox |
| 6,539,247 B2 | 3/2003 | Spetz |
| 6,549,802 B2 | 4/2003 | Thornton |
| 6,554,760 B2 | 4/2003 | Lamoureux et al. |
| 6,561,967 B2 | 5/2003 | Schmidt |
| 6,569,076 B1 * | 5/2003 | Larsen et al. ............ 600/3 |
| 6,572,525 B1 | 6/2003 | Yoshizumi |
| 6,572,527 B2 | 6/2003 | Steele, Sr. et al. |
| 6,575,888 B2 | 6/2003 | Zamora et al. |
| 6,585,633 B2 | 7/2003 | Vitali et al. |
| 6,595,908 B2 | 7/2003 | Loffler et al. |
| 6,599,231 B1 | 7/2003 | Elliot et al. |
| 6,612,976 B2 | 9/2003 | Rosenthal et al. |
| 6,616,593 B1 | 9/2003 | Elliot et al. |
| 6,616,594 B2 | 9/2003 | Fontayne et al. |
| 6,626,817 B2 | 9/2003 | Luth |
| 6,632,176 B2 | 10/2003 | McIntire et al. |
| 6,638,205 B1 | 10/2003 | Chan et al. |
| 6,638,206 B2 | 10/2003 | Green et al. |
| 6,639,237 B2 | 10/2003 | Pedersen et al. |
| 6,648,811 B2 | 11/2003 | Sierocuk et al. |
| 6,656,106 B2 | 12/2003 | Schmidt |
| 6,656,107 B1 | 12/2003 | Pedersen et al. |
| 6,669,621 B2 | 12/2003 | O'Hara et al. |
| 6,669,622 B2 | 12/2003 | Reed et al. |
| 6,679,824 B1 | 1/2004 | Reed et al. |
| 6,682,471 B2 | 1/2004 | Stelle, Sr. et al. |
| 6,689,043 B1 | 2/2004 | McIntire et al. |
| 6,709,381 B2 | 3/2004 | Munro, III |
| 6,716,156 B2 | 4/2004 | Menuhr et al. |
| 6,723,037 B2 | 4/2004 | Hamazaki et al. |
| 6,726,617 B1 | 4/2004 | Schmidt |
| 6,746,661 B2 | 6/2004 | Kaplan |
| 6,749,554 B1 | 6/2004 | Snow et al. |
| 6,752,753 B1 | 6/2004 | Hoskins et al. |
| 6,755,775 B2 | 6/2004 | Kalas et al. |
| 6,761,680 B2 | 7/2004 | Terwilliger et al. |
| 6,786,858 B2 | 9/2004 | Terwilliger et al. |
| 6,790,170 B2 | 9/2004 | Moody et al. |
| 6,800,055 B2 | 10/2004 | Amols et al. |
| 6,805,898 B1 | 10/2004 | Wu et al. |
| 6,820,318 B2 | 11/2004 | Terwilliger et al. |
| 6,837,844 B1 | 1/2005 | Ellard et al. |
| 6,846,283 B2 | 1/2005 | Green et al. |
| 6,905,455 B2 | 6/2005 | Rapach et al. |
| 6,911,000 B2 | 6/2005 | Mick et al. |
| 6,926,657 B1 | 8/2005 | Reed et al. |
| 6,969,344 B2 | 11/2005 | Drobnik et al. |
| 6,989,543 B2 | 1/2006 | Drobnik et al. |
| 7,008,367 B2 | 3/2006 | Visscher et al. |
| 7,060,020 B2 | 6/2006 | Terwilliger et al. |
| 7,074,291 B2 | 7/2006 | Terwilliger et al. |
| 7,083,566 B2 | 8/2006 | Tornes et al. |
| 7,094,198 B2 | 8/2006 | Terwilliger et al. |
| 7,211,039 B2 | 5/2007 | Lamoureux et al. |
| 7,267,643 B2 | 9/2007 | Koster et al. |
| 7,322,928 B2 | 1/2008 | Reed et al. |
| 7,497,818 B2 | 3/2009 | Terwilliger et al. |
| 7,601,113 B2 | 10/2009 | Lebovic et al. |
| 2001/0047185 A1 | 11/2001 | Satz |
| 2002/0066824 A1 | 6/2002 | Floyd et al. |
| 2002/0188195 A1 * | 12/2002 | Mills .................. 600/431 |
| 2003/0084988 A1 | 5/2003 | Terwilliger et al. |
| 2003/0092958 A1 | 5/2003 | Terwilliger et al. |
| 2003/0153804 A1 * | 8/2003 | Tornes et al. ............ 600/7 |
| 2003/0181794 A1 | 9/2003 | Rini et al. |

| | | | |
|---|---|---|---|
| 2003/0191355 | A1 | 10/2003 | Ferguson |
| 2004/0024453 | A1 | 2/2004 | Castillejos |
| 2004/0109823 | A1 | 6/2004 | Kaplan |
| 2004/0111004 | A1* | 6/2004 | Loffler et al. ............ 600/7 |
| 2004/0158117 | A1 | 8/2004 | Drobnik et al. |
| 2004/0158118 | A1 | 8/2004 | Drobnik et al. |
| 2004/0225174 | A1 | 11/2004 | Fuller et al. |
| 2005/0049490 | A1 | 3/2005 | Mills |
| 2005/0261541 | A1 | 11/2005 | Henderson et al. |
| 2006/0052654 | A1 | 3/2006 | Drobnik et al. |
| 2006/0063960 | A1 | 3/2006 | Wissman et al. |
| 2006/0094983 | A1 | 5/2006 | Burbank et al. |
| 2006/0121080 | A1 | 6/2006 | Lye et al. |
| 2006/0177379 | A1 | 8/2006 | Asgari |
| 2007/0224234 | A1 | 9/2007 | Steckel et al. |
| 2007/0238983 | A1 | 10/2007 | Suthanthiran |

FOREIGN PATENT DOCUMENTS

| | | |
|---|---|---|
| EP | 0 466 681 B1 | 1/1992 |
| WO | WO 00/64538 | 2/2000 |
| WO | WO 00/61229 | 10/2000 |
| WO | WO 2008/106586 | 9/2008 |

OTHER PUBLICATIONS

Merrick et al., "Seed Fixity in the Prostate/Periprostatic Region Following Brachytherapy," IJROBP vol. 46(1): pp. 215-220 (2000).

Poggi et al., "Marker Seed Migration in Prostate Localization," IJROBP, vol. 56(5): pp. 1248-1251 (2003).

Tapen et al., "Reduction of Radioactive Seed Embolization to the Lung Following Prostate Brachtherapy," IJROBP, vol. 42(5): pp. 1063-1067 (1998).

Meiller R., "Advances May Improve Prostate Cancer Treatment," Board of Regents of the University of Wisconsin System; <http://www.news.wisc.edu/11899.html>, 3 pages (Dec. 1, 2005).

Alvaro Martinez, et al; "Sterilization of $^{125}$I Seeds Encased in Vicryl Sutures for Permanent Interstitial Implantation"; Intl. J. Radiation Oncology Biol. Phys. vol. 5, pp. 411-413; Pergamen Press Ltd., 1979.

Van't Riet, "Ultrasonically Guided Transperineal Seed Implantation of the Prostate: Modification of the Technique and Qualitative Assessment of Implants", Intl. J. Rad. Onc. Biol. Phys. 24(3): 555-558 (1992).

Middleton et al., "Synthetic Biodegradable Polymers as Medical Devices", Med. Plas. Biomat. (Mar. 1998).

http://investor.mentorcorp.com/news/20010122-32414.cfm, "Mentor Acquires Breakthrough Brachytherapy Technology" (Jan. 25, 2002).

Webster's II New Riverside University Dictionary, p. 191, 1984.

Medi-Physics brochure entitled I-125 Seeds. No. 6711, Medi-Physics, Inc. Arlington Heights Il. 60004, USA; Revised. Oct. 1999, 2 pages.

Medi-Physics brochure entitled I-125 Seeds. No. 7000; Medi-Physics, Inc. Arlington Heights Il. 60004, USA; Revised. Oct. 1999, 2 pages.

Amersham Health; "EchoSeed™"; http://www.amershamhealth-us.com/echoseed/ printed Nov. 19, 2003.

Amersham Health; "Rapid Strand Indications" Http;//www.amershamhealth-us.com/products/index.htp?a=i&i=38; printed Nov. 19, 2003.

Amersham Health; OncoSeed™ (Iodine-125 Seeds) http://www.amershamhealty-us.com/oncoseed/; printed Nov. 19, 2003.

RadioMed: Innovative Products for Radiation, "The Visicoil Advantage . . . for Image Guided Radiation Therapy," http://www.radiomed.com/visicoil/, at lease as early as Aug. 2003.

Oncura, "RapidStrandR$_x$: The Logical Choice for Improved Dosimetry," Ocura Inc., Plymouth Meeting, PA, Apr. 2005.

* cited by examiner

ECHOGENIC SPACERS AND STRANDS

FIELD OF THE INVENTION

This invention relates to radiotherapy. More particularly, it relates to strands for use in brachytherapy, and to echogenic spacers that are used to space radioactive seeds within such strands, while increasing the ultrasound visibility of the strands.

BACKGROUND

In interstitial radiation therapy, a tumor can be treated by temporarily or permanently placing small, radioactive seeds into or adjacent the tumor site. This can be accomplished by implanting loose seeds in the target tissue, or by implanting in the target tissue seeds that are connected to one another by a bio-absorbable material.

To implant loose seeds, an applicator device (e.g., a MICK® applicator or the like) that includes a needle is often used. A stylet is initially fully extended through a bore in the needle and the needle is inserted into a patient in an area where a row of loose seeds are to be implanted. The stylet is then retracted from the needle, enabling a loose seed from a magazine to enter the bore of the needle. The stylet is then pushed against the loose seed, forcing the seed through the bore of needle and into the target tissue. After a first seed has been implanted, the needle is withdrawn from the patient's body by a particular distance so that a next seed to be implanted is spaced apart from the first seed. Then, the stylet is again retracted to enable the next seed from the magazine to be positioned for movement into the needle. The stylet is then advanced through the needle to force the next seed into the target tissue at a desired distance away from the first seed. This procedure is repeated for subsequent seed implants. Additional details of this implantation technique and the applicator used to perform this technique can be found in U.S. Pat. No. 5,860,909, which is incorporated herein by reference.

In the above technique, loose seeds are deposited in a track made by the needle. However, when the needle is withdrawn, there is a tendency for the seeds to migrate in that track resulting in improper distribution of the seeds. Additionally, after implantation, the loose seeds are dependent on the tissue itself to hold each individual seed in place. This may result in the loose seeds migrating over time away from the initial site of implantation. Such migration of seeds is undesirable from a clinical perspective, as this may lead to underdosing or overdosing of a tumor or other diseased tissue and/or exposure of healthy tissue to radiation. The loose seeds may also rotate or twist from the original orientation at which the seeds were implanted. This is also undesirable from a clinical perspective, because the radiation pattern of the seeds may be directional, thereby causing underdosing or overdosing of a tumor or other diseased tissue and/or exposure of healthy tissue to radiation. Further complicating the implantation of loose seeds is the fact that the seeds are small, because they need to fit in small bore needles to prevent excessive tissue damage. Due to their small size and high seed surface dose, the seeds are difficult to handle and to label, and can easily be lost. In addition, the above described technique for implantation of individual loose seeds is time consuming.

Because of the disadvantages of using loose seeds, many physicians prefer using elongated members (often referred to as strands) that contains multiple seeds spaced from one another at desired increments. Such strands are capable of being loaded into an introducer needle just prior to the implant procedure, or they may be pre-loaded into a needle. Implantation of strands is less time consuming than implanting loose seeds. Additionally, because the seeds in the strands are connected to one another by a bio-absorbable material, there is less of a tendency for the seeds to migrate and/or rotate after implantation.

There are numerous techniques for making strands that include multiple seeds. For example, such strands can be made using a bio-absorbable material, with the seeds and rigid teflon spacers between the seeds inserted into the material. Needles loaded with the seeds in the carrier bio-absorbable material are sterilized or autoclaved causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., International Journal of Radiation Oncology, Biology and Physics, Vol. 24, No. 3, pp. 555-558, 1992, which is incorporated herein by reference. Such rigid implants have many drawbacks, including not having the ability to flex with the tissue over the time that the bio-absorbable material dissolves. More specifically, as the tissue or glands shrink back to pre-operative size, and thus as the tissue recedes, a rigid elongated implant does not move with the tissue, but remain stationary relative to the patient. The final locations of the seeds relative to the tumor are thus not maintained and the dosage of the radioactive seeds does not meet the preoperative therapy plan. Accordingly, there is a desire to provide a strand of seeds that is capable of moving with tissue or glands as they shrink back to pre-operative size, thereby enabling the seeds to meet a preoperative therapy plan.

In another technique, disclosed in U.S. Pat. No. 5,460,592, which is incorporated herein by reference, seeds are held in a woven or braided bio-absorbable carrier such as a braided suture. The carrier with the seeds laced therein is then secured in place to form a suitable implant. This braided assembly exhibits many drawbacks, as and when the braided assembly is placed into the target tissue. The needle that carries the braided strand assembly must be blocked at the distal end to prevent body fluids from entering the lumen. If body fluid reaches the braided strand assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided strand assembly causes the braid to expand and jam inside the lumen of the needle. Finally, if the braided strand is successfully expelled from the needle, the relative spacing of the seeds may not be maintained, if the braided material has collapsed. Accordingly, there is also a desire to provide a strand of seeds that can be implanted without causing jamming of a needle, and that after implantation the strand maintain the desired spacing of the seeds.

It is also desirable for a strand of seeds to be echogenic, i.e., be visible using ultrasound imaging, so that the implant can be visualized during implantation and during post operative visits to a physician. Techniques have been developed for making the seeds themselves more echogenic. For example, U.S. Pat. No. 6,632,176 suggests that seeds can be roughened, shaped or otherwise treated to improve the ultrasound visibility of the seeds. However, it is desirable that an entire strand be visible, not just the seeds therein. It has been suggested that the particles of materials such as glass, silica, sand, clay, etc. be mixed in with the bio-absorbable material to make the strand assembly of seeds more visible to ultrasound. However, the additions of such particles may effect the integrity of the strand. Additionally, such particles may irritate tissue after the bio-absorbable material has been absorbed. Further, it may be desirable to simply minimize the volume of materials that are not going to be absorbed by the body. Also, because it may be difficult to control the distribution of such particle, strand including such particles may not be uniformly visible by ultrasound.

Another technique that has been suggested to increase the ultrasound visibility of a strand of seeds is to introduce air bubbles into the bio-absorbable material during the manufacture of the strand, since air is a strong reflector of ultrasound energy having an inherent impedance many times greater than body tissue. This can be accomplished during the cooling stage of a molding process used to produce the strand, as disclosed in U.S. patent application Ser. No. 10/035,083, filed May 8, 2003, which is incorporated herein by reference. More specifically, during the cooling stage, the mold is placed in a vacuum chamber and the air in the chamber is evacuated. This causes the entrapped air in the mold to come out of solution from the polymer, and as the mold cools, this air is entrapped within the cooling polymer in the form of minute bubbles suspended in the plastic. A potential problem with this technique, however, is the inability to control the placement and size of the air bubbles. Thus, a strand including such air bubbles may not be uniformly visible by ultrasound. Accordingly, there is also a desire to improve the ultrasound visibility of a strand of seeds.

SUMMARY OF THE INVENTION

Embodiments of the present invention relate to an apparatus for use in separating radioactive seeds from one another within a strand for use in brachytherapy. In accordance with an embodiment, the apparatus includes a spacer, which is preferably bio-absorbable. A hollow helical chamber extends axially through the spacer, to increase the ultrasound visibility of the spacer.

Embodiments of the present invention also relate a strand for use in brachytherapy that includes a plurality of radioactive seeds with the spacers separating the seeds from one another. At least one of the spacers, and preferably all of the spacers, include a hollow helical chamber that extends axially through the spacer, to increase the ultrasound visibility of the strand within which the spacers are located.

In accordance with an embodiment of the present invention, the spacer is made from one or more string (e.g., three strings) of material wound to form an elongated helical structure having an outer circumferential surface and an inner circumferential surface. The inner circumferential surface forms an outer surface of the hollow helical chamber that extends axially through the spacer. If the desire is for the spacer to be bio-absorbable, then the strings used to make the spacer are made from a bio-absorbable material.

The one or more string of material can be wound around a wire or mandrel, heated and then cooled, to thermoset the string(s) in the helical structure. The wire or mandrel can then be removed, resulting in the hollow helical chamber extending axially through the center of the structure. The structure can then be cut into appropriate sizes to form the spacers that are used to separate radioactive seeds from one another within a strand.

Alternatively, rather than winding the one or more strings around a wire or mandrel, the one or more strings can be wound around a further string that is not removed from the resulting helical structure. In such embodiment, if more than one string is wound around a central string, a plurality of hollow helical chambers will extend axially through the structure. For example, if three strings are wrapped around a central string, then there will be three distinct hollow helical chambers that extend axially through the structure. The structure can then be cut into appropriate sizes to form the spacers that are used to separate radioactive seeds from one another within a strand.

In accordance with an embodiment, like a tightly wound spring, the above described spacers will be generally axially rigid and radially flexible. Accordingly, a strand that is made using such spacers should be generally axially rigid and radially flexible, which is desirable.

This summary is not intended to be a complete description of the invention. Other features, aspects, objects and advantages of the invention can be obtained from a review of the specification, the figures, and the claims.

DETAILED DESCRIPTION

Embodiments of the present invention relate to echogenic spacers that can be used to space seeds from one another at desired increments within an elongated member (often referred to as a strand) that is used for interstitial radiation therapy. Embodiments of the present invention also relate to an elongated member (i.e., a strand) that includes such echogenic spacers. Additionally, embodiments of the present invention also relate to methods of making such spacers, and to methods of making an elongated member with such spacers. Strands, seeds, and echogenic spacers may be referred to herein generally or specifically as implants; however, an implant can include strands, seeds, echogenic spacers, and any other objected implantable at a surgical site. Implants are not intended to be limited to those structures described with specificity in the description below.

Figure 1A:
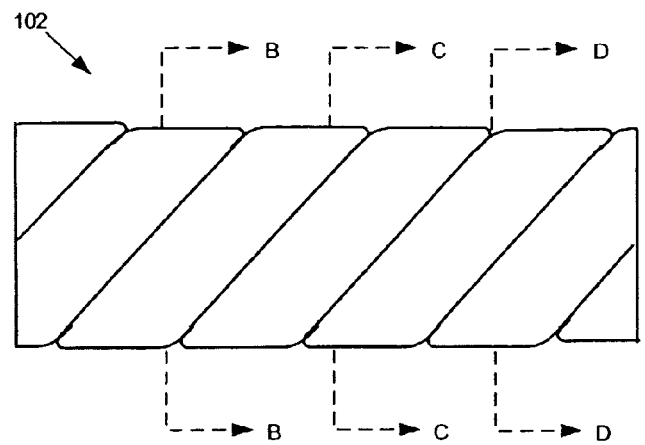
FIG. 1A is a side view of an echogenic spacer, according to an embodiment of the present invention.
Figures 1B, 1C, 1D:
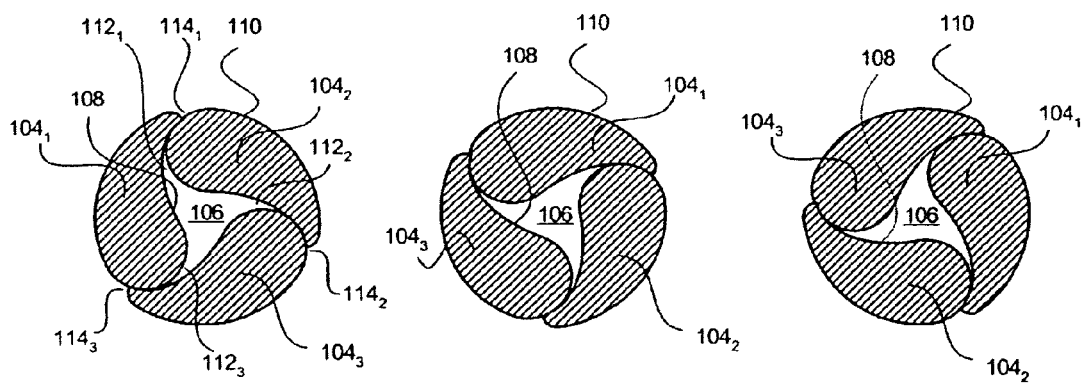
FIGS. 1B, 1C and 1D are, respectively, views of cross-sectional slices of the spacer shown in FIG. 1A, along lines B-B, C-C and D-D.

FIG. 1A shows a side view of a spacer 102, according to an embodiment of the present invention. Three cross sectional views of the spacer 102 are shown in FIGS. 1B, 1C and 1D. As can be seen from the cross sectional views, the spacer 102 is made up of three strings $104_1$, $104_2$ and $104_3$ that twist about a hollow chamber 106. Because the three strings $104_1$, $104_2$ and $104_3$ twist about the hollow chamber 106, an outer surface 108 of the hollow chamber 106 is helical, and more specifically in this embodiment a triple helical. The spacer includes an outer circumferential surface 110 and an inner circumferential surface, with the inner circumferential surface of the spacer being the outer surface 108 of the hollow chamber 106. As shown in FIG. 1B, the inner circumferential surface of the spacer (i.e., the outer surface 108 of the hollow chamber 106) includes three helical grooves $112_1$, $112_2$ and $112_3$, and the outer circumferential surface 110 include three helical grooves $114_1$, $114_2$ and $114_3$, with each of the grooves being formed where the strings $104_1$, $104_2$ and $104_3$ meet one another.

In accordance with an embodiment of the present invention, the strings $104_1$, $104_2$ and $104_3$ are made of a polymeric bio-absorbable material. In one specific embodiment, the strings $104_1$, $104_2$ and $104_3$ are lengths of suture material that can be purchased from Ethicon, Inc., of Somerville, N.J., under the trademark MONOCRYL® (polyglycoprone 25). A list of other possible materials for the strings $104_1$, $104_2$ and $104_3$ are provided below. The diameter of each string is, for example, between 0.005 and 0.020 inches, with a preferably diameter of about 0.012 inches. However, other diameters are possible.

In accordance with an embodiment of the present invention, the spacer 102 is manufactured by twisting the three strings $104_1$, $104_2$ and $104_3$ around a fixed wire or mandrel. The three strings $104_1$, $104_2$ and $104_3$ in their twisted arrangement are then heated, and then cooled, such that the strings $104_1$, $104_2$ and $104_3$ thermal set in the twisted configuration. The wire or mandrel is then pulled out of the center, leaving a structure that is made up of three twisted strings of polymeric bio-absorbable material, with its hollow center having the triple helix outer surface 108. The structure is then cut to appropriate sizes, to produce spacers with improved ultrasound visibility. Like a tightly wound spring, such spacers will be generally axially rigid and radially flexible. Accordingly, a strand that is made using such spacers should be generally axially rigid and radially flexible, which is desirable.

Figure 2:
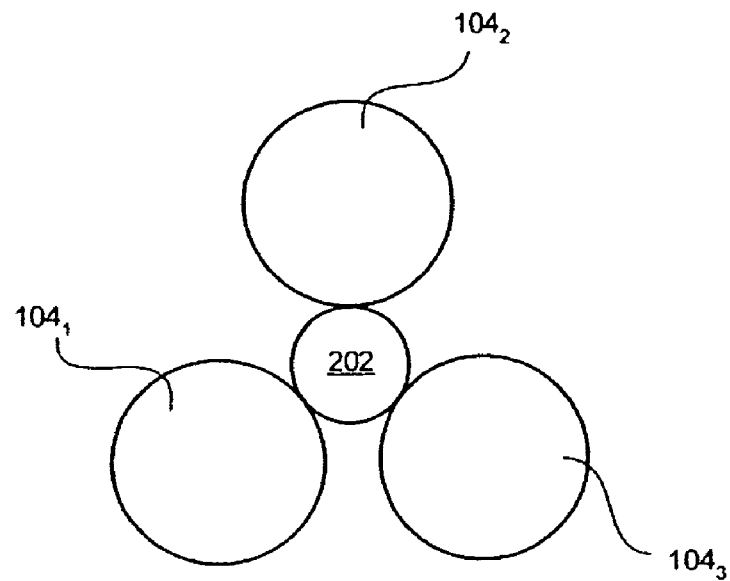
FIG. 2 is an end view of three strings and a wire/mandrel that are used to produce an echogenic spacer in accordance with an embodiment of the present invention.

FIG. 2, which is an end view of the three strings $104_1$, $104_2$ and $104_3$ prior to their twisting, shows that the three strings $104_1$, $104_2$ and $104_3$ can be initially evenly spaced around a wire or mandrel 202, with the centers of the strings $104_1$, $104_2$ and $104_3$ preferably being about 120 degrees apart from one another. Also shown in FIG. 2 is that a cross section of each string $104_1$, $104_2$ and $104_3$ can be generally circular, but this need not be the case.

Figure 3:
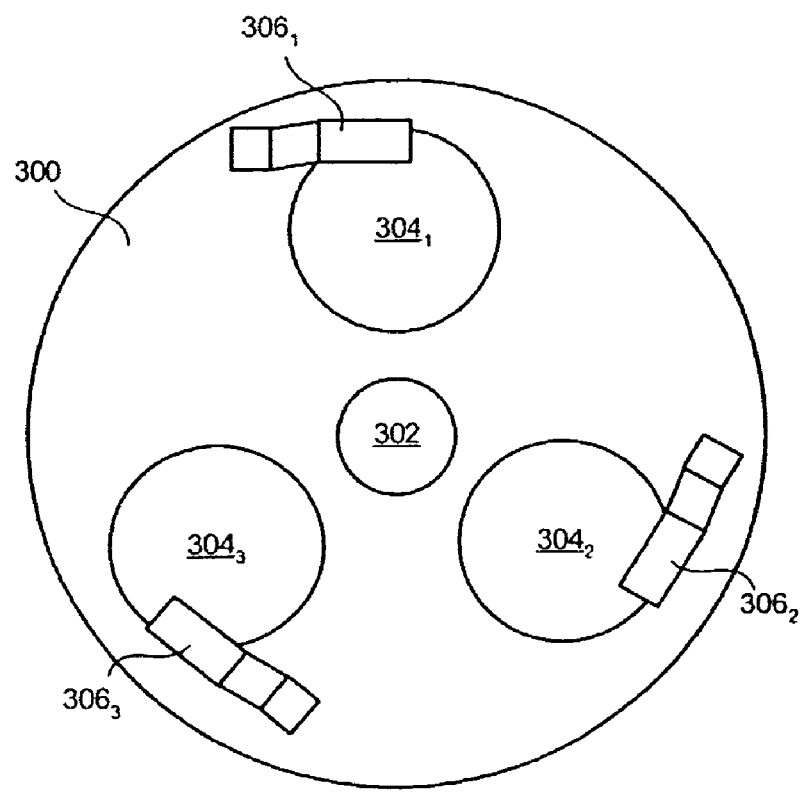
FIG. 3 illustrates an exemplary rotating structure that can be used to produce an echogenic spacer, according to an embodiment of the present invention.

In a specific implementation, the wire or mandrel 202 is threaded or fed through a hole in the center of a rotating structure, and both longitudinal ends of the wire or mandrel 202 are fixedly attached (e.g., clamped) within a fixture, such that the wire or mandrel is pulled taut, and such that the rotating structure can rotate about the wire or mandrel. An exemplary rotating structure 300 that can be used is shown in FIG. 3. In addition to have a hole 302 in its center, the rotating structure 300 also includes three openings $304_1$, $304_2$ and $304_3$ that are about 120 degrees apart from one another and spaced around the hole 302. Each of these three openings $304_1$, $304_2$ and $304_3$ is configured to accept one of the three strings $104_1$, $104_2$ and $104_3$. A diameter of the rotating structure is, e.g., about 0.75 inches. The diameters of the center opening 302 and other openings $304_1$, $304_2$ and $304_3$ should be slightly greater than the wire/mandrel or stings to be placed through the openings.

The strings $104_1$, $104_2$ and $104_3$ are fixed (e.g., clamped) at one end of the fixture, in the arrangement shown in FIG. 2. The other end of the strings $104_1$, $104_2$ and $104_3$ are fed through corresponding openings $304_1$, $304_2$ and $304_3$ in the rotating structure 300, shown in FIG. 3. Flat springs $306_1$, $306_2$ and $306_3$, or some other means, are used to hold the ends of the strings within the holes $304_1$, $304_2$ and $304_3$. Such springs $306_1$, $306_2$ and $306_3$ should allow for some slippage of the strings $104_1$, $104_2$ and $104_3$ when they shrink during heating, which is described below. Preferably about ten percent of each string $104_1$, $104_2$ and $104_3$ extends past the rotating structure 300 and hangs freely, so that the strings $104_1$, $104_2$ and $104_3$ do not release from the flat springs $306_1$, $306_2$ and $306_3$ when they are eventually heated and shrink. Once in this arrangement, the rotating structure 300 is turned in one direction (clockwise or counterclockwise) to thereby twist the strings $104_1$, $104_2$ and $104_3$ around the wire or mandrel 202. As the rotating structure 300 is turned, each string $104_1$, $104_2$ and $104_3$ twists around the wire or mandrel 202, causing the rotating structure 300 to be pulled toward the fixed ends of the strings $104_1$, $104_2$ and $104_3$.

In one embodiment, the wire or mandrel 202 has a diameter of about 0.007 inches, and each string $104_1$, $104_2$ and $104_3$ has an initial diameter of about 0.012 inches. With such dimensions, in accordance with an embodiment, the strings $104_1$, $104_2$ and $104_3$ are twisted around the wire or mandrel 202 such that the combined pitch of the strings is between 20 and 30 turns per inch, and preferably about 25 turns per inch. This would mean that each individual string $104_1$, $104_2$ and $104_3$ winds around the wire or mandrel about 6 to 10 times per inch, and preferably about 8 times per inch. This will result in the overall length of the twisted sting structure being about one-third of the original length of the strings $104_1$, $104_2$ and $104_3$. For example, if the strings $104_1$, $104_2$ and $104_3$ are initially 12 inches in length, the length of the structure made up of the twisted strings $104_1$, $104_2$ and $104_3$ will be about 4 inches.

After the strings $104_1$, $104_2$ and $104_3$ are twisted around the wire or mandrel 202 to achieve a desired pitch, the rotating structure 300 is then fixed in place, e.g., using another clamp, so that the strings $104_1$, $104_2$ and $104_3$ don't unwind. The entire fixture can then be placed in an oven or otherwise exposed to heat, to thereby heat the strings $104_1$, $104_2$ and $104_3$. Preferably, the twisted strings $104_1$, $104_2$ and $104_3$ are placed in the oven while the oven is at least 100 degrees F. lower than the desired temperature to which the strands will be exposed. This desired temperature, which is dependent on the material from which the strings $104_1$, $104_2$ and $104_3$ are made, is a temperature at which the strings 104 will shrink, but not melt. For example, if the strings $104_1$, $104_2$ and $104_3$ are made from MONOCRYL® (polyglycoprone 25), then the strings $104_1$, $104_2$ and $104_3$ (and the fixture that holds the strings in place) should be placed in an oven when the oven is less than 360 degrees F., and then the oven should be raised to a temperature of about 460 degrees F. At this temperature, the strings $104_1$, $104_2$ and $104_3$ will shrink in diameter and length, forming tight spirals around the wire or mandrel. A small amount of fusion may occur between the strings $104_1$, $104_2$ and $104_3$, but this is not necessary. The flat springs $306_1$, $306_2$ and $306_3$ will allow the strings $104_1$, $104_2$ and $104_3$ to slip a little through their openings $304_1$, $304_2$ and $304_3$ in the structure 300, without releasing the strings $104_1$, $104_2$ and $104_3$.

The entire fixture, with the rotated strings $104_1$, $104_2$ and $104_3$ held in place, is then cooled. Once cooled, the strings $104_1$, $104_2$ and $104_3$ are thermo set in their tightly wound configuration. At that point, the strings $104_1$, $104_2$ and $104_3$ are released from the fixture, and the wire or mandrel 102 is removed, thereby leaving an elongated structure that is made up of tightly wound strings $104_1$, $104_2$ and $104_3$, with a hollow center chamber having an outer surface that is helical, and in this specific implementation a triple helix. This elongated structure is then cut into desired lengths to form spacers, which are used to space radioactive seeds from one another within an elongated therapeutic member known as a strand. The use of these spacers within a strand will be described in more detail below.

The inner diameter of the resulting spacer 102 is dependent upon the diameter of the wire or mandrel 202 around which the strings $104_1$, $104_2$ and $104_3$ were wound. Thus, if the wire or mandrel had a diameter of 0.007 inches, then the inner diameter of the spacer 102 (which defines the size of the hollow chamber 106) will be about 0.007 inches. The outer diameter of the spacer 102 will be dependent on the diameter of the wire or mandrel 202 around which the strings $104_1$, $104_2$ and $104_3$ were wound, the diameter of each string $104_1$, $104_2$ and $104_3$, and the amount by which the strings shrink during the thermal setting process. Assuming the wire or mandrel 202 has a diameter of about 0.007 inches, and the diameter of each string $104_1$, $104_2$ and $104_3$ is about 0.012 inches, then the outer diameter of the spacer 102 will be about 0.026 inches.

Ultrasound visibility is highly dependent upon the angular orientation of a surface with respect to the ultrasound inducer that is used for imaging. Generally, a smooth surface will act as a mirror, scattering ultrasound waves in a numerous directions unless the angle between the sound and the surface is very close to 90 degrees. Accordingly, if surfaces of a spacer were relatively smooth, such surfaces would reflect ultrasound waves in a generally fan shaped conical pattern that spanned a large spatial angle, only giving a strong ultrasound reflections when imaged at an angle very close to 90 degrees. In contrast, in the present invention, because the outer surface 108 of the hollow chamber 106 of the spacer 102 is helical, at least a portion of the surface 108 will likely be substantially 90 degrees from incoming ultrasound waves. Accordingly, the spacers of the present invention avoid angular dependence of the reflected ultrasound.

As mentioned above, the spacers 102 of the present invention can be used to increase ultrasound visibility of a strand used in brachytherapy. More specifically, such a strand typically includes a plurality of radioactive seeds that are spaced apart from one another at desired intervals. These intervals can be selected to be any distance or combination of distances that are optimal for the treatment plan of a patient. The strand is preferably axially flexible such that it can be bent back upon itself in a circle without kinking. However, the strand preferably has sufficient column strength along its longitudinal axis so that the strand can be urged out of a hollow needle without the strand folding upon itself. The spacers 102 of the present invention can be used to maintain the desired spacings between seeds within the strand, when the strand is being made, while allowing the stand to be axially rigid and radially flexible. This will be better understood from the following discussion of how such strands can be made.

Figure 4A:
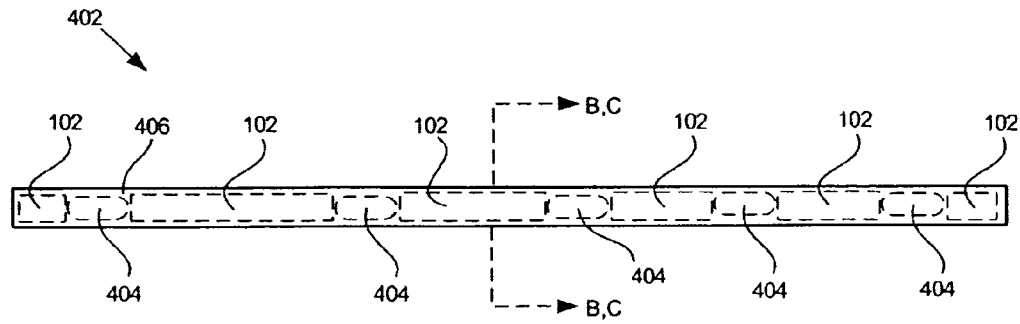
FIG. 4A illustrates a side view of a strand for use in brachytherapy that includes echogenic spacers of the present invention.

A side view of an exemplary strand 402, according to an embodiment of the present invention, is shown in FIG. 4A. The strand 402 includes a plurality of radioactive seeds 404 that are spaced apart from one another at desired intervals using spacers 102 of the present invention. Encapsulating the spacers 102 and the seeds 404 is a material 406. In one embodiment, the encapsulating material 406 is a bio-absorbable material marketed under the trademark VICRYL® (polyglactin 910, also known as PGA), which can be purchased from Ethicon, Inc., of Somerville, N.J. A list of other possible materials for the material 406 are provided below.

Figure 4B:
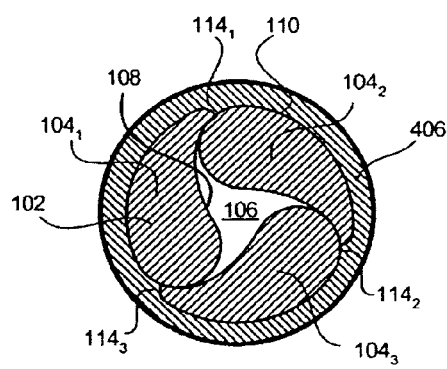
FIG. 4B illustrates a cross sectional view of the strand of FIG. 4A.

A cross sectional views of the strand 402 is shown in FIG. 4B. As can be seen in this view, even after the spacers 102 are encapsulated within the material 406, the spacers 102 still have a hollow helical chamber 106 having an outer surface 108 including three helical grooves $114_1$, $114_2$ and $114_3$. However, the helical grooves $114_1$, $114_2$ and $114_3$ on the outer surface 110 of the spacers 102 may or may not be filled in by the material 406. More specifically, in FIG. 4B, the helical grooves $114_1$, $114_2$ and $114_3$ on the outer surface 110 of the spacer 102 are shown as being filled in. However, it is possible that the helical grooves $114_1$, $114_2$ and $114_3$ on the outer surface 110 of the spacer 102 are not filled in, thereby resulting in three additional hollow helical chambers, which will further increase the ultrasound visibility of the strand 402.

The strand 402 can be manufacture in various manners. For example, the strand 402 can be manufactured using a hollow tube or VICRYL® "sock" by pushing the seeds and spacing elements into the tube or a molding processes, such as, but not limited to, compression molding or injection molding. In one example, the plurality of radioactive seeds 404 are inserted into a tube or "sock" and the spacers 102 are placed between the seeds 404 to maintain a desired spacing between the seeds 404. The spacers 402 can be of the same length, or of different lengths, if the preoperative therapeutic plan so specifies. The spacers 402 can be made available in the plurality of different lengths, or the spacers can be cut to their proper lengths.

Preferably the encapsulating material 406 melts at a temperature significantly greater than 250 degrees F., thereby allowing the strand 402 to be steam sterilized before implantation.

As shown in FIG. 4, spacers 102 can also be placed near the distal ends of the strand 402, to thereby increase the ultrasound visibility of the ends of the strand 402.

Figure 5:
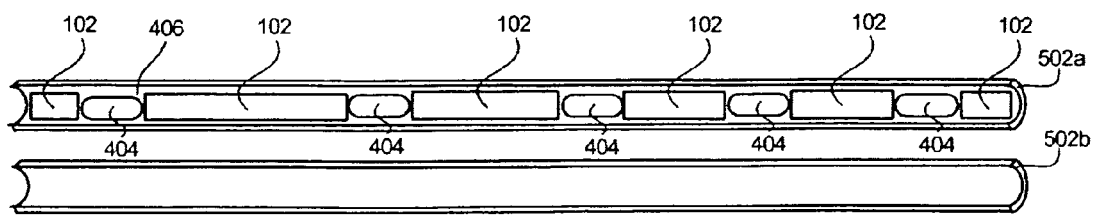
FIG. 5 illustrates a pair of half-shells within which radioactive seeds and echogenic spacers of the present invention can be placed to form a strand for use in brachytherapy.

Referring now to FIG. 5, in another embodiment a strand 402 can be constructed using a pair of pre-formed elongated members 502a and 502b of bio-absorbable material that are shaped like half-shells. Such half-shells 502a and 502b are described in additional detail in U.S. Pat. No. 6,761,680, which is incorporated herein by reference. The seeds 404 and spacers 102 are placed within one of half-shells 502a. The second half-shell 502b is then mated with the first half-shell 502a, and the half-shells 502a and 502b are heated, fusing the half-shells 502a and 502b together and fixing the seeds 404 and spacers 102 inside. The material of the half-shells 502a and 502b should have a lower melt temperature than the spacers 102, so that the half-shells can be fused without melting the spacers 102.

In another embodiments, a strand can be made by inserting (i.e., pushing) the seeds 404 and spacers 102 through an opening in one end of an elongated hollow tube of bio-absorbable material. Additional details of a seed pusher that can be used in this process are described in U.S. Pat. No. 6,761,680, which was incorporated herein by reference above.

In still another embodiment, a strand can be made by inserting the seeds 404 and spacers 102 into a tube of braded bio-absorbable material. Additional details of such a braded bio-absorbable tube are described in U.S. Pat. No. 5,460,592, which is incorporated herein by reference.

In each of the above described embodiments for manufacturing a strand 402 for use in brachytherapy, and encapsulating material 406 encapsulates the seeds 404 and spacers 102 within the strand 402. After the strand is manufactured, it can then be inserted into a patient for use in interstitial radiation therapy. An exemplary device that can be used to perform such insertion into a patient will now be described with reference to FIG. 6.

Figure 6:
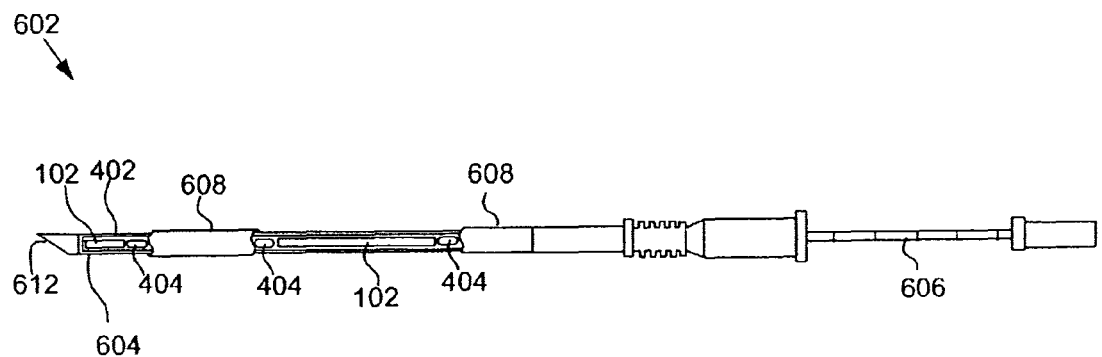
FIG. 6 illustrates an exemplary brachytherapy device that can be used to implant strands of the present invention into a patient.

FIG. 6 is a side view of a brachytherapy device 602, which includes a needle 604 and a stylet 606. The needle 604 is shown partially broken away and has a sheath component 608, and is loaded with a strand 402 of the present invention. A beveled end 612 of the needle 604 is plugged with a bio-compatible substance 610 to prevent fluids and tissue from entering the needle 604 and coming in contact with the strand 402 prior to the placement of the strand 402 at its desired location (e.g., adjacent a tumor). The plug 610 can be made out of a bone wax or can be made of one of the bio-absorbable polymers or copolymers listed below. Further the plug 610 can be an end of the member or strand 402 that is heated and reflowed after the strand is inserted into the needle 604. In operation, the stylet 606 is inserted into the needle 604 until it meets the strand 402. Then the needle 604 is inserted into a patient at the desired site. The strand 402 is gradually extruded from the needle 604 via the static force of the stationary stylet 606, as the needle 604 is pulled back and removed from the patient.

In the embodiments described above, the spacers 102 were described as being made from three strings $104_1$, $104_2$ and $104_3$. While it is preferred that at least three strings $104_1$, $104_2$ and $104_3$ are used to produce the echogenic spacers of the present invention, it is also within the scope of the present invention that a single string, or two strings be used. It is also within the scope of the present invention that more than three strings may be used to make a spacer. Regardless of the number of strings, spacers can be made by twisting the strings around a wire or mandrel, thermal setting the twisted string structure, and then removing the wire or mandrel, as was described above with reference to FIGS. 2 and 3. Changing the number of strings used to make the spacer 102 will simply change the number of helical grooves in the inner circumferential surface (i.e., the outer surface of the hollow chamber) and the number of helical grooves in the outer circumferential surface of the spacer.

Figure 7:
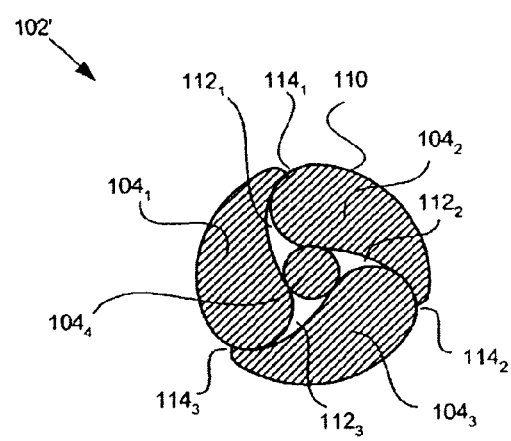
FIG. 7 illustrates a cross section of an echogenic spacer according to another embodiment of the present invention.

In accordance with another embodiment, rather than twisting one or more strings around a wire or mandrel 202, the one or more strings (e.g., three strings $104_1$, $104_2$ and $104_3$) can be wrapped around a further string $104_1$, $104_2$ and $104_3$, which is not removed from the spacer. An exemplary cross section of a spacer 102' made in this manner is shown in FIG. 7. As can be seen from FIG. 7, this spacer 102' is made by twisting three strings $104_1$, $104_2$ and $104_3$ around a center string $104_4$. A spacer made in this manner does not include a hollow center, since the center string (string $104_4$ in FIG. 7) is not removed. Rather, a helical air chamber is formed by each of the helical grooves $112_1$, $112_2$ and $112_3$, providing for good ultrasound visibility.

It is preferable that the strings used to make spacers 102 and the encapsulating material 406 used to make strands 402 (with the spacer 102 and seeds 404 therein) are bio-absorbable.

Example types of materials that are bio-absorbable include, but are not limited to, synthetic polymers and copolymers of glycolide and lactide, polydioxanone and the like. Such polymeric materials are more fully described in U.S. Pat. Nos. 3,565,869, 3,636,956, 4,052,988 and European Patent Publication No. 0030822, all of which are incorporated herein by reference. Specific examples of bio-absorbable polymeric materials that can be used to produce embodiments of the present invention are polymers made by Ethicon, Inc., of Somerville, N.J., under the trademarks MONOCRYL® (polyglycoprone 25), MAXON® (Glycolide and Trimethylene Carbonate), VICRYL® (polyglactin 910, also known as PGA) and PDS II™ (polydioanone).

Other exemplary bio-absorbable materials include poly (glycolic acid) (PGA) and poly(-L-lactic acid) (PLLA), polyester amides of glycolic or lactic acids such as polymers and copolymers of glycolate and lactate, polydioxanone and the like, or combinations thereof. Such materials are more fully described in U.S. Pat. No. 5,460,592 which is hereby incorporated by reference. Further exemplary bio-absorbable polymers and polymer compositions that can be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly[L(–)lactide-co-glycolide] suitable for use as absorbable sutures; U.S. Pat. No. 3,297,033 which discloses the use of compositions comprising polyglycolide homopolymers as absorbable sutures; U.S. Pat. No. 2,668, 162 which discloses compositions comprising high molecular weight polymers of glycolide with lactide; U.S. Pat. No. 2,703,316 which discloses compositions comprising polymers of lactide and copolymers of lactide with glycolide; U.S. Pat. No. 2,758,987 which discloses compositions comprising optically active homopolymers of L(–) lactide i.e. poly L-Lactide; U.S. Pat. No. 3,636,956 which discloses compositions of copolymers of L(–) lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bio-absorbable semi-crystalline depsipeptide polymers; U.S. Pat. No. 5,264,540 which discloses bio-absorbable aromatic polyanhydride polymers; and U.S. Pat. No. 4,689,424 which discloses radiation sterilizable absorbable polymers of dihydric alcohols. If desired, to further increase the mechanical stiffness of the molded embodiments of the present invention, bio-absorbable polymers and polymer compositions can include bio-absorbable fillers, such as those described in U.S. Pat. No. 4,473,670 (which is incorporated by reference) which discloses a composition of a bio-absorbable polymer and a filler comprising a poly(succinimide); and U.S. Pat. No. 5,521,280 (which is incorporated by reference) which discloses bio-absorbable polymers and a filler of finely divided sodium chloride or potassium chloride.

Where the materials are bio-absorbable, the bio-absorbable material should preferably be absorbed in living tissue in a period of time of from about 70 to about 120 days, but can be manufactured to be absorbed anywhere in a range from 1 week to 1 year, depending on the therapeutic plan for a specific patient. Preferably the bio-absorbable material is selected to absorb about when the half-life of the radioactive seeds is reached. The materials should also be bio-compatible, whether or not they are bio-absorbable.

The term polymer, as used herein, is also meant to include copolymers. Table 1 below provides examples of bio-absorbable polymers suitable for use in producing embodiments of the present invention, along with specific characteristics (e.g., melting points) of the various polymers. A further discussion of such bio-absorbable polymers can be found in an article by John C. Middleton and Arthur J. Tipton entitled "Synthetic Biodegradable Polymers as Medical Devices," published March 1998 in Medical Plastics and Bio-materials, which article is incorporated herein by reference.

TABLE 1

Biodegradable polymers, properties and degradation time

| POLYMER | MELTING POINT (° C.) | GLASS-TRANSITION TEMP (° C.) | MODU-LUS Gpa$^a$ | DEGRA-DATION TIME (MONTHS)$^b$ |
|---|---|---|---|---|
| PGA | 225-230 | 35-40 | 7.0 | 6 to 12 |
| LPLA | 173-178 | 60-65 | 2.7 | >24 |
| DLPLA | Amorphous | 55-60 | 1.9 | 12 to 16 |
| PCL | 58-63 | (−65)-(−60) | 0.4 | >24 |
| PDO | N/A | (−10)-0 | 1.5 | 6 to 12 |
| PGA-TMC | N/A | N/A | 2.4 | 6 to 12 |
| 85/15 DLPLG | Amorphous | 50-55 | 2.0 | 5 to 6 |
| 75/25 DLPLG | Amorphous | 50-55 | 2.0 | 4 to 5 |
| 65/35 DLPLG | Amorphous | 45-50 | 2.0 | 3 to 4 |
| 50/50 DLPLG | Amorphous | 45-50 | 2.0 | 1 to 2 |

$^a$Tensile or flexural modulus.
$^b$Time to complete mass loss. Rate also depends on part geometry.

The seeds 404 included in the strands 402 can be of various types having low energy and low half-life such as Iodine seeds, known as I-125 seeds, including a welded titanium capsule containing iodine 125 absorbed on a silver rod, or Palladium 103 seeds. Exemplary dimensions of a seed 102 are 0.18 inches in length and 0.0315 inches in diameter. Exemplary seeds are listed below in Table 2, but embodiments of the present invention should not be limited to the seeds listed therein.

TABLE 2

Seed Manufacturers and Common Types of Seeds

| MANUFACTURER | SEED NAME |
|---|---|
| IODINE$^{125}$ | |
| Amersham 6711 | ONCOSEED ® |
| Amersham 6733 | ECHOSEED ® |
| Amersham 7000 | RAPID STRAND ® |
| North American Scientific | IOGOLD ™ |
| Best Industries | BEST IODINE-125 ™ |
| Bebig | SYMMETRA ™ |
| Mills Biopharmaceuticals | PROSTASEED ™ |
| Syncor | PHARMASEED ™ |
| International Isotopes | ISOSTAR ™ |
| Implant Sciences | I-PLANT ™ |
| International Brachytherapy | INTERSOURCE-125 ® |
| IsoAid | ADVANTAGE I-125 ® |
| Source Tech | STM1251 ™ |
| DRAXIMAGE, Inc. | BRACHYSEED ® |
| PALLADIUM$^{103}$ | |
| North American Scientific | PD GOLD ™ |
| Theragenics | THERASEED 200 ® |
| Best Industries | BEST PALLADIUM-103 ™ |
| International Brachytherapy | INTERSOURCE 103 ® |

Alternatively, seeds 404 can be manufactured using iridium 192, cesium 131, gold 198, yttrium 90 and/or phosphorus 32. Further radioactive isotopes used to manufacture seeds are not limited to these examples, but can include other sources of different types of radiation.

In addition it is to be understood that other types of seeds can be used. For example, seeds such as those described in U.S. Pat. No. 6,248,057, which is incorporated herein by reference, can be used with the present invention. These seeds include radiation delivery devices, drug delivery devices, and combinations of radiation and drug delivery devices in the form of beads, seeds, particles, rods, gels, and the like. These particular seeds are absorbable wherein the radiation member or drug delivery member is contained within, for example, absorbable polymers such as those listed below or in the above-referenced patent. In such seeds, the bio-absorbable structure can have a predefined persistence which is the same as or substantially longer than a half life of the radioactive member contained in the bio-absorbable structure. These above bio-absorbable seeds can be used in the same manner as the seeds described herein with respect to the invention. The present invention can be used to improve untrasound visibility of Fudicial Markers (i.e. Gold Markers) and other non-radioactive elements used in radiation treatment. The invention can be encapsulated at one or both ends of the marker.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention. For example, one could produce the same effect of the linear helical coil or other shaped airspace within the spacer by molding each piece or extruding then cutting the desired length.

What is claimed is:

1. An apparatus adapted to separate treatment seeds for use in brachytherapy from one another, the apparatus comprising:
 a spacer having an axial length, the spacer including at least two strings twisted together to define an outer surface and an inner surface of the spacer; and
 a chamber within the inner surface having a generally helical shape defined by the two or more strings extending along at least a portion of the axial length, the chamber adapted to improve ultrasound visibility.

2. The apparatus of claim 1, wherein
 the chamber extends axially through an axial center of the spacer; and
 the chamber includes at least one helical groove extending into the inner surface from the axial center.

3. The apparatus of claim 1, further comprising:
 a center string extending axially through an axial center of the spacer; and
 the chamber is helically arranged about the center string.

4. The apparatus of claim 1, wherein the spacer includes at least two strings that are twisted about a center string.

5. The apparatus of claim 1, wherein the chamber extends along substantially the entire axial length.

6. A strand for use in brachytherapy, comprising:
 polymeric encapsulating material;
 a seed disposed within the polymeric encapsulating material;
 a spacer disposed within the polymeric encapsulating material and arranged adjacent to the seed, the spacer including at least two strings twisted together to define an outer surface and inner surface of the spacer and having an axial length; and
 a chamber having a generally helical shape defined by the inner surface extending along at least a portion of the axial length, the chamber adapted to improve ultrasound visibility.

7. The strand of claim 6, wherein:
the chamber extends axially through an axial center of the spacer; and
the chamber includes at least one helical groove extending into the inner surface from the axial center.

8. The strand of claim 6, further comprising:
a center string extending axially through an axial center of the spacer; and
wherein the chamber is helically arranged about the center string.

9. The strand of claim 8, wherein the at least two strings are twisted about the center string.

10. The strand of claim 6, wherein at least two strings are twisted such that the inner and outer surfaces of the spacer have generally helical shapes.

11. The strand of claim 6, wherein:
the spacer includes three strings twisted about the center string; and
three helical chambers are formed between the spacer and the center string.

12. The strand of claim 6, wherein the chamber is adapted to house one of a gas and a liquid having an ultrasonic reflectivity greater than an ultrasonic reflectivity of patient tissue.

13. The strand of claim 6, wherein the seed is a first seed; and further comprising:
a second seed disposed within the polymeric encapsulating material such that the spacer is arranged between the first seed and the second seed; and
the axial length of the spacer extends generally between the first seed and the second seed.

14. The strand of claim 6, wherein the polymeric encapsulating material is an elongated hollow tube.

15. A spacer adapted to separate treatment seeds for use in brachytherapy from one another, the spacer comprising:
at least two strings helically arranged around a cylindrical space;
wherein the at least two strings each have a length such that when the at least two strings are helically arranged, the arrangement has an axial length adapted to substantially define a space between two treatment seeds; and
the at least two helical grooves formed by the at least two strings, at least two helical grooves extending from the cylindrical space, wherein the at least two helical grooves and the cylindrical space form a chamber that improves ultrasound visibility of the spacer.

16. The spacer of claim 15, wherein the at least two strings are provided with persistent structural cohesiveness through thermal setting.

17. The spacer of claim 15, wherein the at least two strings include three strings twisted together to define three distinct helical grooves.

18. The spacer of claim 15, wherein the chamber contains one of a gas and a liquid having an ultrasonic reflectivity greater than an ultrasonic reflectivity of patient tissue.

19. The spacer of claim 15, wherein the chamber has an axial length and the at least two helical grooves extend along substantially the entire axial length.

20. The spacer of claim 15, wherein the at least two helical grooves extend along substantially the entire axial length.

21. The strand of claim 15, wherein the chamber has an axial length and the at least two helical grooves extend along substantially the entire axial length.

22. A spacer adapted to separate treatment seeds for use in brachytherapy from one another, the spacer comprising:

a center string having an axial length;
at least two outer strings helically arranged about the center string so that the center string is enclosed along the axial length by the at least two outer strings; and
at least two helical grooves formed by the at least two strings, the at least two helical grooves forming corresponding at least two chambers to improve ultrasound visibility of the spacer.

23. The spacer of claim 22, wherein the at least two outer strings are provided with persistent structural cohesiveness through thermal setting.

24. The spacer of claim 22, wherein the spacer includes three strings twisted together to define three distinct helical grooves forming three distinct chambers.

25. The spacer of claim 22, wherein said corresponding at least two chambers contain one of a gas and a liquid having an ultrasonic reflectivity greater than an ultrasonic reflectivity of patient tissue.

26. A strand for use in brachytherapy, comprising:
polymeric encapsulating material;
a seed disposed within the polymeric encapsulating material;
a spacer having an axial length disposed within the polymeric encapsulating material and arranged adjacent to the seed, the spacer including:
at least two strings helically arranged about a cylindrical space; and
at least two helical grooves formed by the at least two strings, the at least two helical grooves extending from the cylindrical space, wherein the at least two helical grooves and the cylindrical space form a chamber that improves ultrasound visibility of the spacer.

27. The strand of claim 26, wherein the at least two strings are provided with persistent structural cohesiveness through thermal setting.

28. The strand of claim 26, wherein the at least two strings include three strings twisted together to define three distinct helical grooves.

29. The strand of claim 26, wherein the chamber contains one of a gas and a liquid having an ultrasonic reflectivity greater than an ultrasonic reflectivity of patient tissue.

30. A spacer adapted to separate treatment seeds for use in brachytherapy from one another, the spacer comprising:
three polymeric strings helically arranged around a cylindrical space so that the spacer has an outer circumferential surface and an inner circumferential surface, wherein the three polymeric strings each have a length such that when the three polymeric strings are helically arranged, the arrangement has an axial length adapted to substantially define a space between two treatment seeds; and
three helical grooves, each helical groove being formed in the inner circumferential surface where two of the three polymeric strings abut, wherein the three helical grooves extend from the cylindrical space so that the three helical grooves and the cylindrical space form a single chamber that improves ultrasound visibility of the spacer.

31. The spacer of claim 30, further comprising:
a center string extending through the cylindrical space; and
wherein the three grooves form three chambers that improve ultrasound visibility of the spacer.

\* \* \* \* \*